United States Patent [19]

Zajaczkowski

[11] Patent Number: 5,236,428
[45] Date of Patent: Aug. 17, 1993

[54] ABSORBENT ARTICLE HAVING AUXILLARY ABSORBENT MEMBER HAVING STANDING LEG GATHERS

[75] Inventor: Peter Zajaczkowski, Auburn, Wash.

[73] Assignee: Paragon Trade Brands, Inc., Federal Way, Wash.

[21] Appl. No.: 853,928

[22] Filed: Mar. 19, 1992

[51] Int. Cl.$^5$ ............................................. A61F 13/15
[52] U.S. Cl. .............................. 604/385.2; 604/385.1; 604/383
[58] Field of Search .............. 604/383, 385.1, 397–398, 604/378, 385.2

[56] References Cited

U.S. PATENT DOCUMENTS

| | | |
|---|---|---|
| 3,825,006 | 7/1974 | Ralph . |
| 3,868,442 | 6/1986 | Sabee . |
| 4,501,587 | 2/1985 | Enloe . |
| 4,795,454 | 1/1989 | Dragoo ............................ 604/385.2 |
| 4,892,528 | 1/1990 | Suzuki et al. ..................... 604/385.2 |
| 4,938,756 | 7/1990 | Salek ................................. 604/368 |
| 5,135,522 | 8/1992 | Fahrenkrug et al. ............. 604/385.1 |

FOREIGN PATENT DOCUMENTS

| | | | |
|---|---|---|---|
| 0439962 | 8/1991 | European Pat. Off. ......... | 604/385.2 |
| 3-198851 | 8/1991 | Japan ................................ | 604/385.2 |
| 3-231660 | 10/1991 | Japan ................................ | 604/385.2 |

Primary Examiner—Randall L. Green
Assistant Examiner—D. Willse
Attorney, Agent, or Firm—Dressler, Goldsmith, Shore, Sutker & Milnamow, Ltd.

[57] ABSTRACT

An absorbent article, illustrated as a disposable diaper, includes a primary absorbent member and an auxiliary absorbent member. The primary absorbent member has an upper liquid-receiving surface area. The auxiliary absorbent member includes a liquid-permeable lower surface region, and a pair of substantially liquid-impermeable upstanding leg gathers in at least a target area of the absorbent article. An attachment arrangement joins the primary and auxiliary absorbent members to position the liquid-permeable lower surface region of the auxiliary absorbent member in liquid-transferring relationship with the upper liquid-receiving surface area of the primary absorbent member.

10 Claims, 2 Drawing Sheets

ABSORBENT ARTICLE HAVING AUXILLARY ABSORBENT MEMBER HAVING STANDING LEG GATHERS

TECHNICAL FIELD

The present invention relates generally to an absorbent article, and more particularly to an absorbent article comprising in combination a primary absorbent member and an auxiliary absorbent member having liquid-impermeable standing leg gathers.

BACKGROUND OF THE INVENTION

The use in absorbent articles of an auxiliary absorbent pad in combination with a primary absorbent pad is well known, for example, such as the so-called "diaper doubler". Such an auxiliary absorbent pad is usually placed atop the primary absorbent pad for the purpose of increasing absorbent capacity.

U.S. Pat. No. 4,501,587, to Enloe, discloses a combination of a main absorbent pad and an auxiliary absorbent pad to increase the absorbent capacity of the front section of the diaper. The main and auxiliary absorbent pads are assembled together within an enclosure.

U.S. Pat. No. 4,938,756, to Salek, describes a two-piece absorbent article. An auxiliary absorbent member is placed atop a primary absorbent member such as a diaper. The auxiliary absorbent member has a liquid transferable undersurface, on which intermittent adhesive is provided for fastening to the primary absorbent member, so that liquids are transferable between the primary and auxiliary absorbent members. The auxiliary absorbent member may be T-shaped to maximize the absorbent capacity of the auxiliary absorbent member, for example, for gender specific diaper use. While this patent construction provides a variety of pad design options, it does not address the barrier characteristics of the construction to prevent overflowing of liquids running along top surfaces of the auxiliary and primary absorbent members.

U.S. Pat. No. 3,386,442, to Sabee, discloses a diaper having liquid impermeable side strips to cover side edges of an enclosed absorbent pad. Similarly, U.S. Pat. No. 3,825,006, to Ralph, shows a diaper including liquid impermeable side flaps which overlap respective opposite side margins of an absorbent pad.

U.S. Pat. No. 4,490,148, to Beckestrom, discloses a diaper having a liquid-impermeable upstanding gathers which improve liquid containment characteristics of the diaper. U.S. Pat. No. 4,795,454, to Dragoo, discloses an absorbent garment including a liquid barrier sheet along each side margin of the article to cover and seal the side edges of the absorbent core. The liquid barrier sheet also has an upstanding portion which is intended to prevent liquid from flowing along a top surface to the edge of the garment.

SUMMARY OF THE INVENTION

An absorbent article embodying the principles of the present invention includes a primary absorbent member and an auxiliary absorbent member. The primary absorbent member has an upper liquid-receiving surface. The auxiliary absorbent member is provided with a pair of substantially liquid-impermeable upstanding leg gathers in at least a target area of the absorbent article to abate passage of liquid transversely thereof. The auxiliary absorbent member further includes a liquid-permeable region at a lower surface thereof. An attachment means joins the primary and auxiliary absorbent members to position the liquid-permeable lower surface of the auxiliary absorbent member in liquid-transferring relationship with the upper liquid-receiving surface of the primary absorbent member.

In the illustrated embodiments, an auxiliary absorbent means of the auxiliary absorbent member is longitudinally shorter than a length of the lower surface of the auxiliary absorbent member, and is positioned toward a front portion of the absorbent article and atop the liquid-permeable region of lower surface. The auxiliary absorbent means may comprise a plurality of separate absorbent members.

In accordance with illustrated embodiments, the liquid-permeable region may comprise one or more holes provided in an otherwise substantially liquid-impermeable lower surface of the auxiliary absorbent member. The liquid-permeable region is preferably positioned in the target area of the absorbent article, (i.e., that area of the article at which liquid is typically discharged by a wearer) in order to rapidly transfer the discharged liquids downwardly therethrough toward the primary absorbent member. Alternatively, the liquid-permeable region may comprise a liquid-permeable hydrophilic region provided in the lower surface of the auxiliary absorbent member.

Other features and advantages of the present invention will become readily apparent from the following detailed description, the accompanying drawings, and the appended claims.

DETAILED DESCRIPTION

Figure 1:
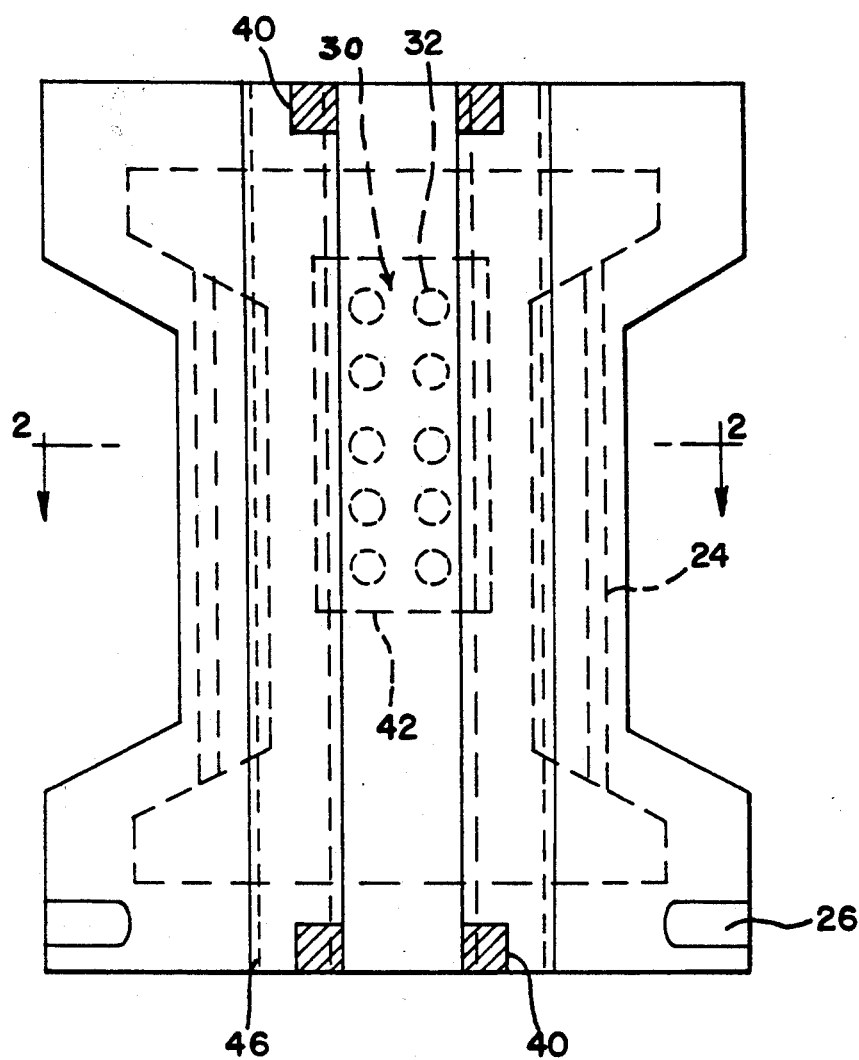
FIG. 1 is a plan view of a disposable diaper embodying the principles of the present invention.

While the present invention is susceptible of embodiment in various forms, there is shown in the drawings and will hereinafter be described presently preferred embodiments, with the understanding that the present disclosure is to be considered as an exemplification of the invention, and is not intended to limit the invention to the specific embodiments illustrated.

Figure 2:
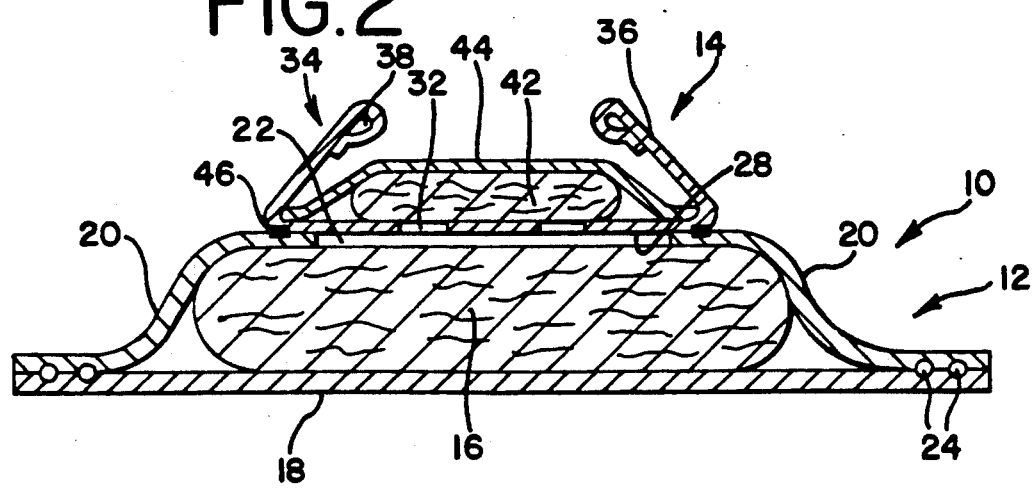
FIG. 2 is a cross-sectional view taken along lines 2—2 of FIG. 1.

With reference now to FIGS. 1 and 2, therein is illustrated an absorbent article 10 embodying the principles of the present invention. It is to be understood that absorbent articles embodying the principles of the present invention can be appropriately sized for use by infants, children and incontinent adults.

Absorbent article 10 comprises a primary absorbent member 12, such as a diaper, and an auxiliary absorbent member 14. Primary absorbent member 12 includes a primary absorbent panel 16, which is hourglass-shaped, as illustrated in FIG. 1, but which may be otherwise shaped, such as rectangular, T-shaped, I-shaped, or otherwise contoured. The absorbent panel preferably comprises an absorbent matrix including comminuted wood pulp, sometimes referred to as pulp fluff, and superabsorbent material, which may comprise superabsorbent polymers or the like. Absorbent matrices comprising blends and/or layers of such superabsorbent materials can be employed. If desired, the superabsorbent material may optionally be more heavily concentrated in specifically selected regions of the absorbent panel. Additionally, an absorbent matrix formed in accordance with U.S. Pat. No. 4,573,988, to Pieniak, comprising a compressed composite absorbent structure including a resilient web of fibers having superabsorbent material incorporated therein, can be used.

Primary absorbent member 12 further includes a backsheet 18 positioned on the side of primary absorbent panel 16 which defines the outer surface of primary absorbent member 12. Backsheet 18 typically comprises a liquid-impermeable material. A wide variety of suitable polymeric film materials can be employed for the backsheet 18, such as a polyethylene sheet having a thickness on the order of 0.0005 to 0.001 inches. Polyethylene terephthalate sheet material having a thickness of approximately 0.0005 to 0.001 inches may alternatively be employed. Composite or laminate sheet materials such as comprising integrated nonwoven fabric and polymeric film layers may also be employed.

Primary absorbent member 12 is further provided with a pair of side marginal sheets 20 which extend along respective opposite side edges of primary absorbent member 12 to cover respective side edges of primary absorbent panel 16. Side marginal sheets 20 are laterally spaced from each other to define therebetween a central liquid-receiving open surface 22 in an upper surface of primary absorbent member 12. Liquid-receiving surface 22 longitudinally crosses a target zone and extends the full length of primary absorbent member 12. Side marginal sheets 20 are preferably hydrophobic or liquid-impermeable to abate liquid flow. Suitable materials are a hydrophobic nonwoven fabric such as polypropylene or polyesters, or impermeable polyolefin film or sheet materials, laminates thereof, and the like. Each side marginal sheet 20 is preferably glued to backsheet 18 by lines of hot melt adhesive.

Elastic members 24, such as elastic strands made from natural or synthetic rubber, are longitudinally placed between side marginal sheet 20 and backsheet 18 along each side edge of primary absorbent member 12 to provide an elastic gather around a wearer's leg.

In order to secure absorbent article 10 in position, adhesive tape fasteners 26, as well known in the art, are provided on the rearward portions of primary absorbent member 12. Each of these fasteners 26 includes a tab-like element having a pressure-sensitive adhesive thereon which, when brought into contact with a landing area associated with the forward, outer waist portion of absorbent article 10, secures absorbent article 10 in position. Primary absorbent member 12 may also be provided with an optional elasticized waistband, as is well known in the art.

Auxiliary absorbent member 14 includes a lower surface 28, which in FIG. 1 is illustrated as having a length substantially coextensive with primary absorbent member 12 and a width corresponding to the distance between the opposite elastic gathers. Lower surface 28 contains a liquid-permeable region 30 which in this particular embodiment comprises a plurality of holes 32 provided in the otherwise liquid-impermeable lower surface 28. Liquid-permeable region 30 is preferably positioned in the target area of absorbent article 10, which is the area at which liquid is typically discharged by the wearer, so as to rapidly transfer liquids downwardly therethrough.

While illustrated as being rectangular, lower surface 28 may be T-shaped, I-shaped, or otherwise contoured.

Auxiliary absorbent member 14 further includes a pair of substantially liquid-impermeable standing leg gathers 34 extending from and upwardly of respective side edges of lower surface 28 to abate passage of liquid transversely of auxiliary absorbent member 14. Each of standing leg gathers 34 comprises a substantially liquid-impermeable flap 36 having an overturned free edge to form a sleeve portion within which a pre-stretched monofilament elastic element 38 is enclosed. Each substantially liquid-impermeable flap 36 may be an extension of lower surface 28, or alternatively may be a separate sheet of material secured to each side edge of lower surface 28. Such material preferably comprises substantially liquid-impermeable plastic film material.

In accordance with the illustrated embodiment, it is presently preferred that the free edge of each substantially liquid-impermeable flap 34 be overturned inwardly toward a longitudinal centerline of auxiliary absorbent member 14, particularly when the longitudinal end portions of each standing leg gather 34 are secured inwardly by securement means such as adhesive 40.

In the illustrated embodiment, each standing leg gather 34 is of a substantially constant width throughout the length of auxiliary absorbent member 14. However, each leg gather may be configured to vary in width, being relatively narrow at front and/or rear waist portions, and relatively wider at the target area of absorbent article 10.

Auxiliary absorbent member 14 further includes an auxiliary absorbent means 42, positioned on top of lower surface 28. The auxiliary absorbent means 42 may be similar in structure to primary absorbent means 16. It is however preferable that auxiliary absorbent means 42 has a lower density than primary absorbent means 16. In the illustrated embodiment, auxiliary absorbent means 42 is longitudinally shorter than the length of lower surface 28 and is positioned toward a front portion of absorbent article 10 and atop liquid-permeable region 30 of lower surface 28, which corresponds to the target area of absorbent article 10. Auxiliary absorbent means 42 may alternatively be otherwise longitudinally placed in auxiliary absorbent member 14 to achieve a zoned absorbency effect. While as illustrated as being rectangular, auxiliary absorbent means 42 may have a generally T-shaped, I-shaped, or any contoured configuration.

Auxiliary absorbent member 14 further includes a liquid-permeable facing or topsheet 44 positioned on top of auxiliary absorbent means 42, with topsheet 44 being adapted for positioning adjacent to the wearer of absorbent article 10. Topsheet 44 is typically made of carded, spunlaced, spunbonded, or thermally-bonded polypropylene or polyester nonwoven fabrics, as is well known in the art.

Absorbent article 10 of the present invention further includes attachment means 46 for combining primary absorbent member 12 and auxiliary absorbent member 14. Specifically, attachment means 46 respectively join standing leg gathers 34 of auxiliary absorbent member 14 to marginal sheets 20 of primary 25 absorbent member 12 to position the liquid permeable lower surface region 30 of auxiliary absorbent member 14 in liquid-transferring relationship with liquid-receiving surface 22 of primary absorbent member 12. Attachment means 46 may be any means as known in the art, including adhesive, heat-sealing and ultrasonic bonding. In a particular embodiment illustrated in FIGS. 1 and 2, respective substantially liquid-impermeable standing leg gathers 34 are longitudinally coextensive with and joined to side marginal sheets 20 by continuous lines of adhesive 46 over the full length of primary absorbent member 12.

Figure 3:
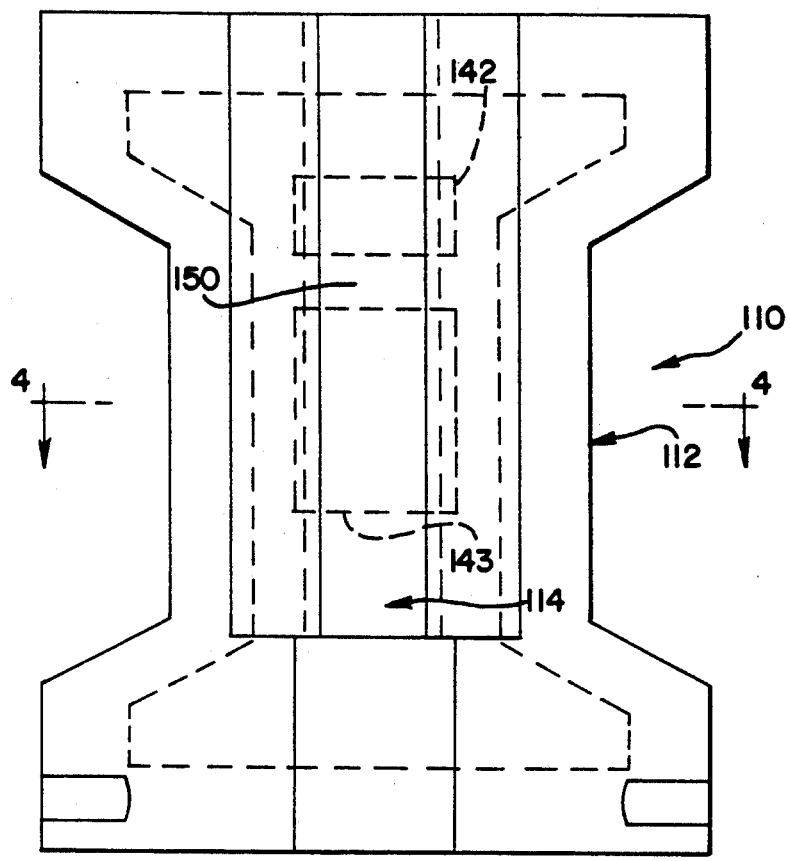
FIG. 3 is a plan view of another disposable diaper embodiment in accordance with the present invention.
Figure 4:
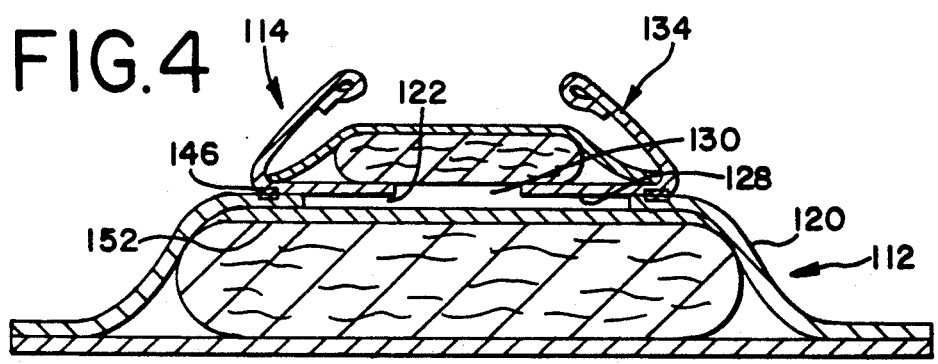
FIG. 4 is a cross-sectional view taken along lines 4—4 of FIG. 3.

FIGS. 3 and 4 illustrate another embodiment of absorbent article in accordance with the present invention. An absorbent article 110 includes an auxiliary absorbent member 114 placed on top of a primary absorbent member 112 by attachment means 146. Auxiliary absorbent member 114 is positioned in about front two-thirds section of absorbent article 110. Auxiliary absorbent member 114 includes in its middle section separate absorbent elements 142, 143 which are longitudinally spaced to each other to form a liquid acquisition area 150 between them in the target zone. Liquid acquisition area 150 is positioned to be placed in the vicinity of the point of liquid discharge by the wearer.

Auxiliary absorbent member 114 further includes a liquid-impermeable lower surface 128 having a central opening to define a liquid-permeable region 130. Liquid-permeable region 130 extends longitudinally the full length of lower surface 128. A pair of substantially liquid-impermeable standing leg gathers 134 extend from respective side edges of lower surface 128 so that they prevent liquid passage transversely of at least the target zone in absorbent article 110.

Primary absorbent member 112 includes a hydrophilic sheet 152, preferably exhibiting liquid-wicking characteristics (such as a tissue layer), extending between opposite side marginal sheets 120 so it is positioned at liquid-receiving surface 122. Liquid-receiving surface 122 is configured to have a larger width than liquid-permeable region 130 of auxiliary absorbent member 114.

Figure 5:
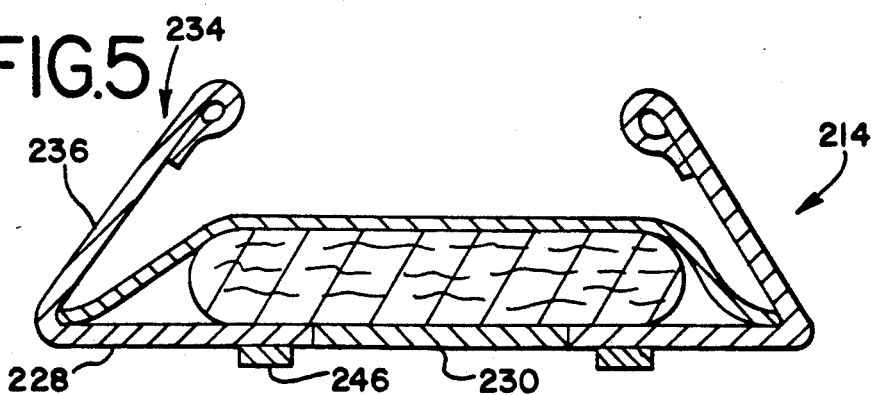
FIG. 5 is a cross-sectional view illustrating another embodiment of the auxiliary absorbent member.

FIG. 5 shows another embodiment of auxiliary absorbent member 214 which includes liquid-permeable region 230 comprising a liquid-permeable fibrous sheet. The fibrous sheet 230 can be joined at each of its opposite side edges to a respective substantially liquid-impermeable flap 236 of standing leg gather 234. An intermittent adhesive 246 is provided for fastening the auxiliary absorbent member to the primary absorbent member. The primary absorbent member may optionally be configured to include a landing zone to releasably receive such intermittent adhesive 246 on each of its side marginal sheets.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. An absorbent article, comprising:
    a primary absorbent member having an upper, liquid receiving surface area;
    a pair of side marginal sheets extending in spaced relationship to each other along respective opposite side edges of said primary absorbent member;
    an auxiliary absorbent member positioned on top of said primary absorbent member and defining a liquid-permeable region at a lower surface thereof;
    a pair of upstanding leg gathers extending upwardly from respective side edges of said lower surface of said auxiliary absorbent member, in at least a target area of said absorbent article to abate passage of liquid transversely of said auxiliary absorbent member, said pair of leg gathers extending from a region between said primary absorbent member and said auxiliary absorbent member; and
    attachment means for respectively joining said upstanding leg gathers to said marginal sheets generally at an upper surface of said primary absorbent member to position said liquid-permeable lower surface region of the auxiliary absorbent member in liquid-transferring relationship with said upper liquid-receiving surface of the primary absorbent member.

2. An absorbent article in accordance with claim 1, wherein:
    said side marginal sheets are hydrophobic.

3. An absorbent article in accordance with claim 1, wherein:
    said auxiliary absorbent member includes an absorbent means which is shorter than a length of said lower surface of the auxiliary absorbent member.

4. An absorbent article in accordance with claim 3, wherein:
    said absorbent means is positioned toward a front portion of the absorbent article.

5. An absorbent article in accordance with claim 3, wherein:
    said absorbent means comprises a plurality of separate absorbent elements spaced from each other.

6. An absorbent article in accordance with claim 1, wherein:
    said lower surface of the auxiliary absorbent member is longitudinally coextensive with said primary absorbent member.

7. An absorbent article in accordance with claim 1, wherein:
    said liquid-permeable lower surface region of the auxiliary absorbent member comprises a liquid-permeable material.

8. An absorbent article in accordance with claim 1, wherein:
    said liquid-permeable region at the lower surface of the auxiliary absorbent member comprises at least one opening defined at said lower surface.

9. An absorbent article in accordance with claim 1, wherein:
    said liquid-permeable region is longitudinally coextensive with said upper liquid-receiving surface of the primary absorbent member.

10. An absorbent article in accordance with claim 1, wherein:
    said liquid-permeable region is transversely coextensive with said upper liquid-receiving surface of the primary absorbent member.

* * * * *